United States Patent [19]

Thead et al.

[11] Patent Number: 4,986,811
[45] Date of Patent: Jan. 22, 1991

[54] APPARATUS AND METHOD FOR SAFELY REMOVING NEEDLES FROM SYRINGES

[75] Inventors: William H. Thead; John C. Evans, both of Atlanta, Ga.

[73] Assignee: Post Medical, Inc., Atlanta, Ga.

[21] Appl. No.: 248,470

[22] Filed: Sep. 23, 1988

[51] Int. Cl.[5] .............................................. A61M 5/32
[52] U.S. Cl. ..................................... 604/110; 206/366
[58] Field of Search ....................... 604/110, 192, 240; 206/366; 220/1 T

[56] References Cited

U.S. PATENT DOCUMENTS

| | | | |
|---|---|---|---|
| 4,667,821 | 5/1987 | Shillington | 206/366 |
| 4,798,587 | 1/1989 | Willoughby et al. | 604/110 |
| 4,807,344 | 2/1989 | Kelson et al. | 206/366 |

FOREIGN PATENT DOCUMENTS 2601512  3/1977  Fed. Rep. of Germany ...... 604/110

Primary Examiner—Stephen C. Pellegrino
Attorney, Agent, or Firm—Jones, Askew & Lunsford

[57] ABSTRACT

A system is disclosed for removing disposable needles from syringes, which requires only one hand to operate and which exposes the user to minimal risk of contact with the contaminated needle. The user inserts the syringe and presses downwardly, whereupon disconnecting gears engaging the collar of the needle unscrew the needle and allow it to drop into a container. Return springs then automatically return the device to its original configuration.

20 Claims, 7 Drawing Sheets

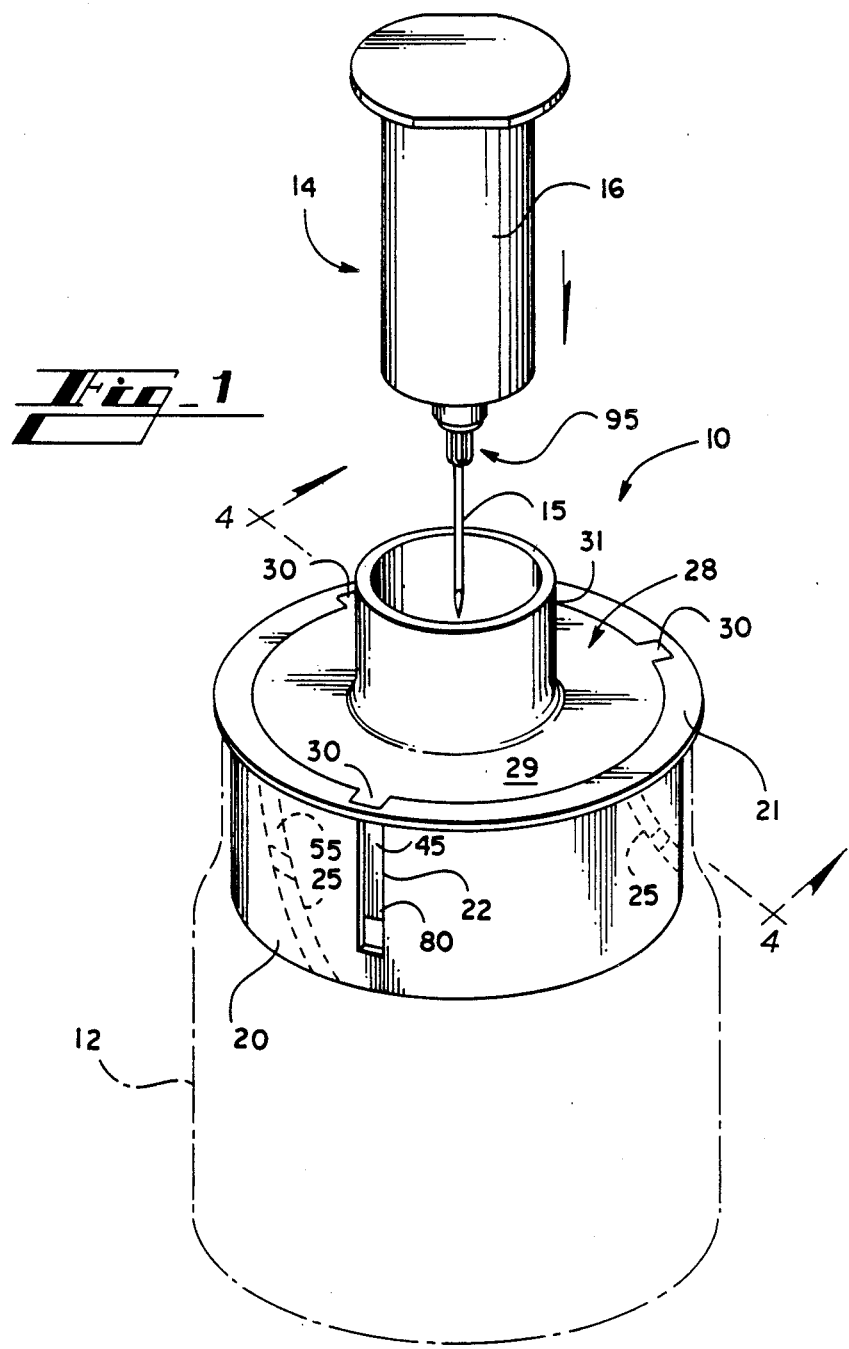
Fig_1

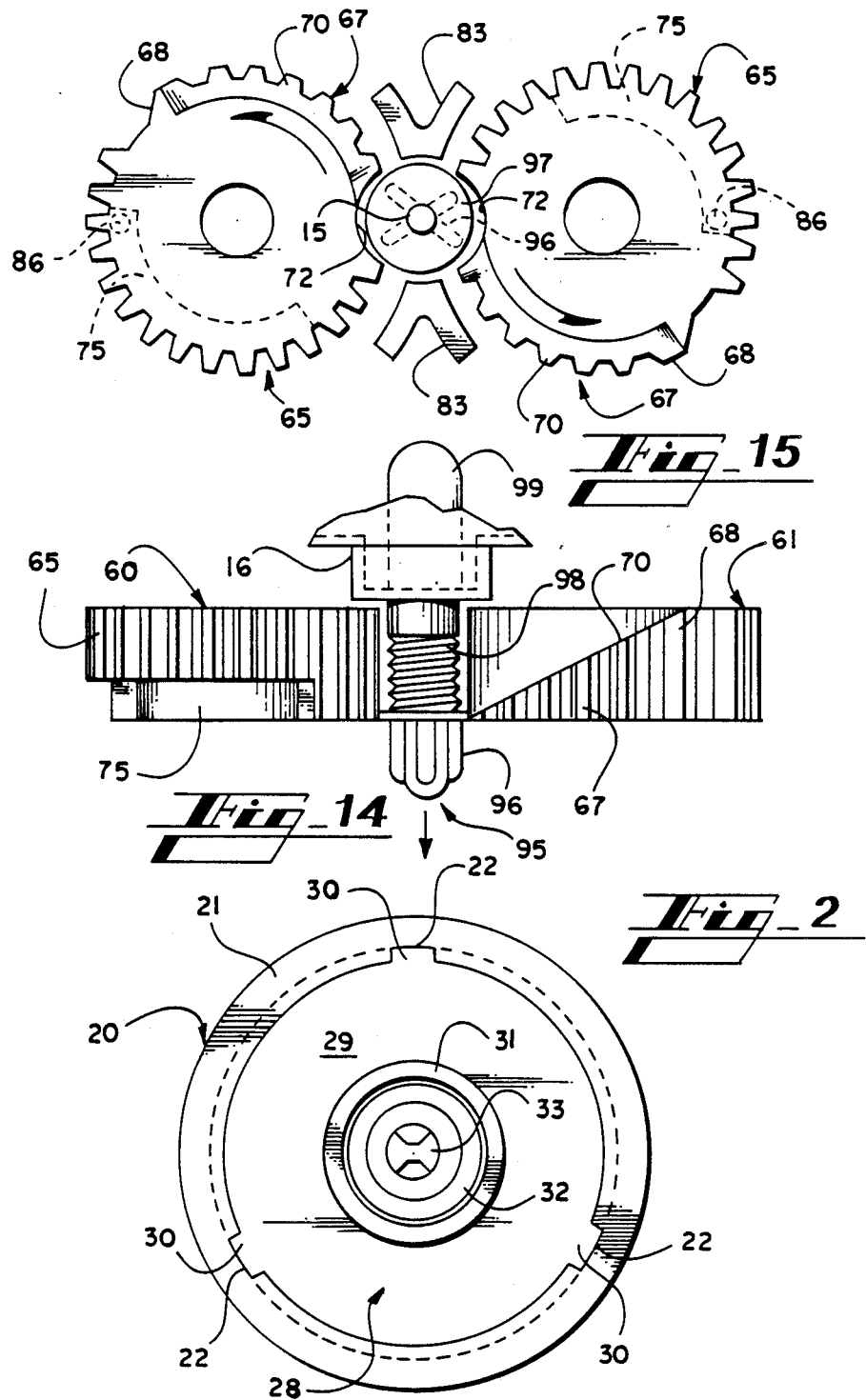

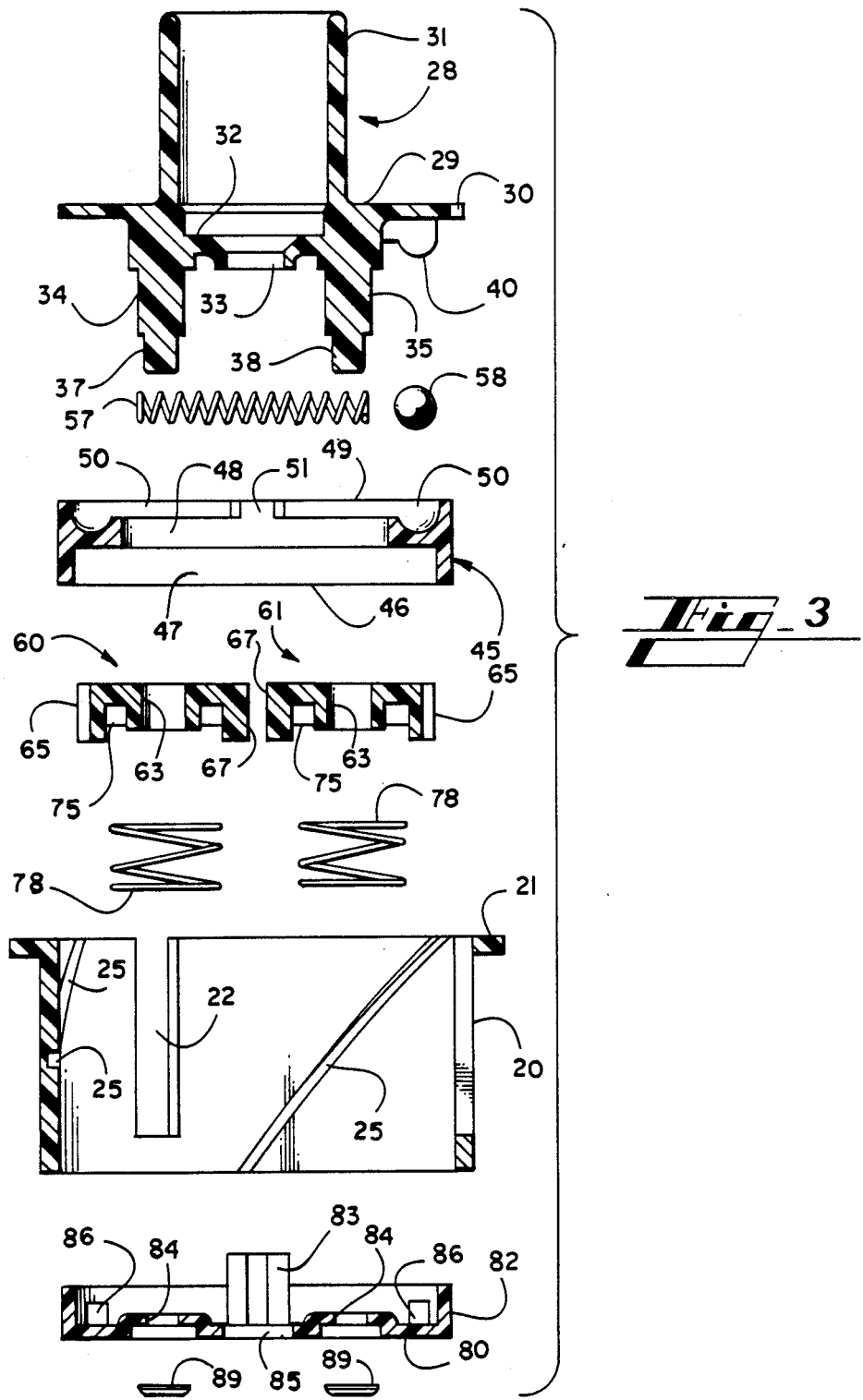
Fig_3

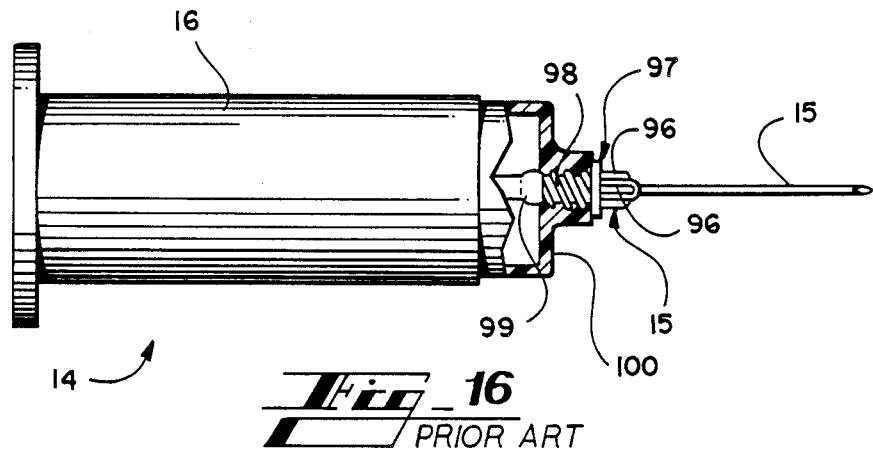
Fig_16 PRIOR ART
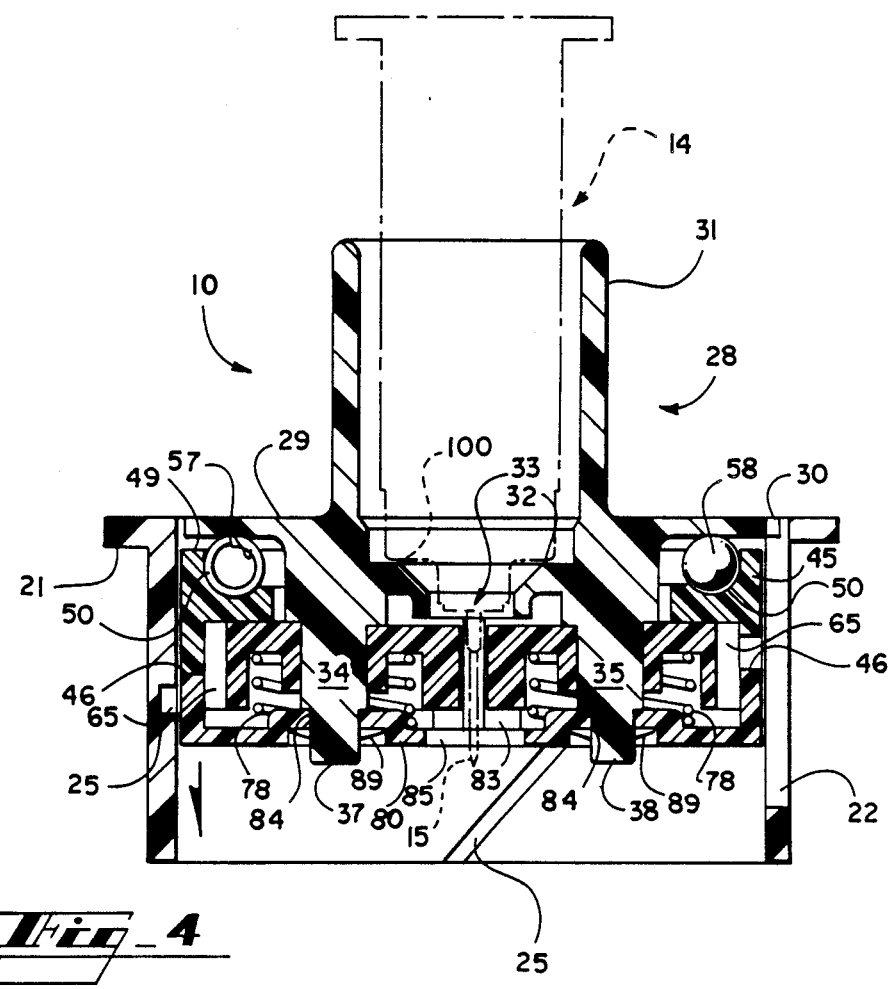
Fig_4

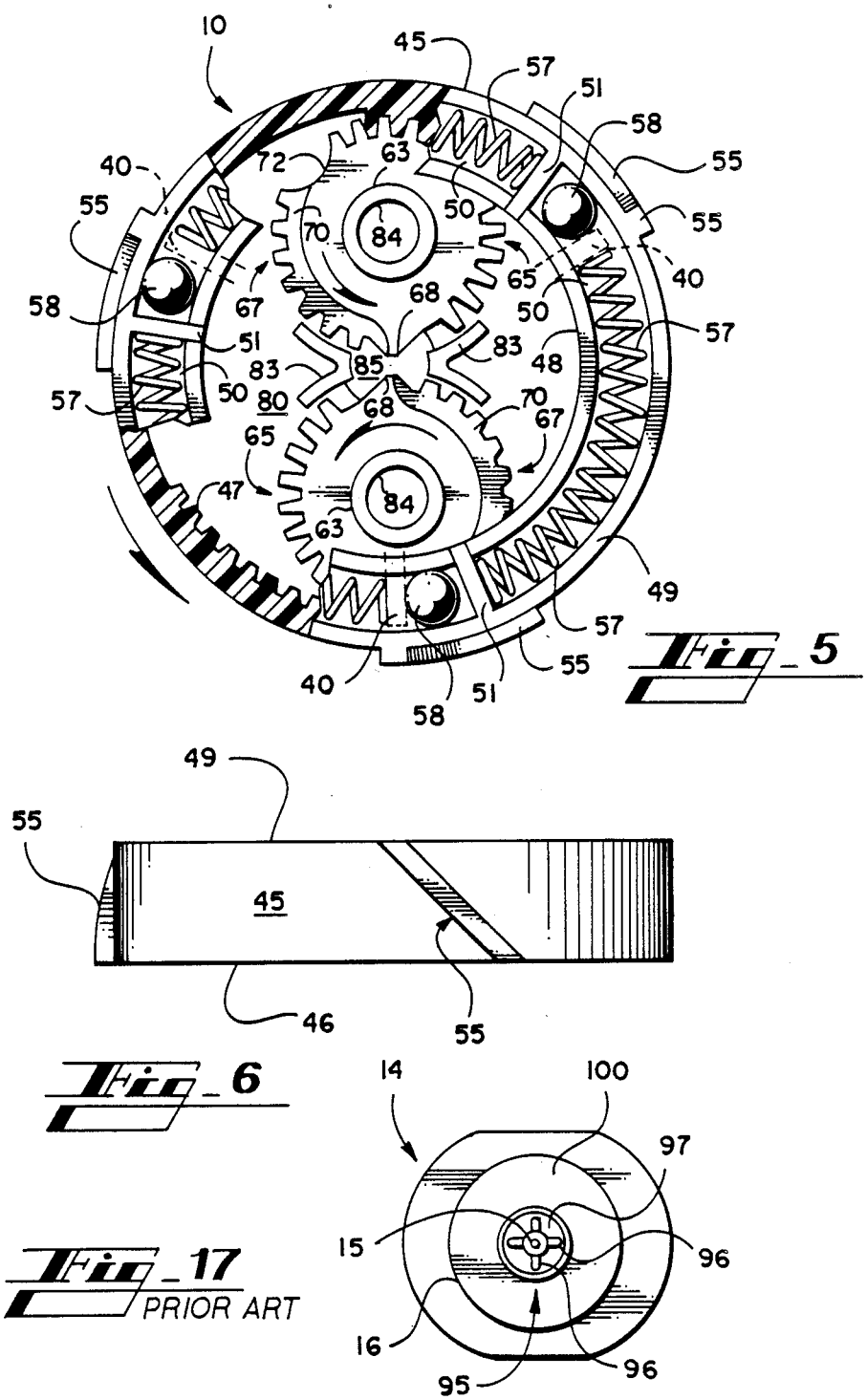

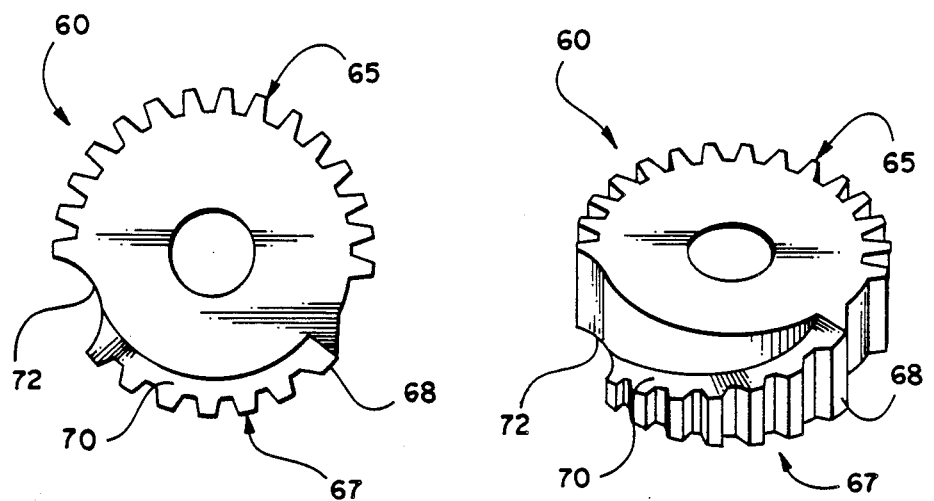
Fig_9   Fig_7
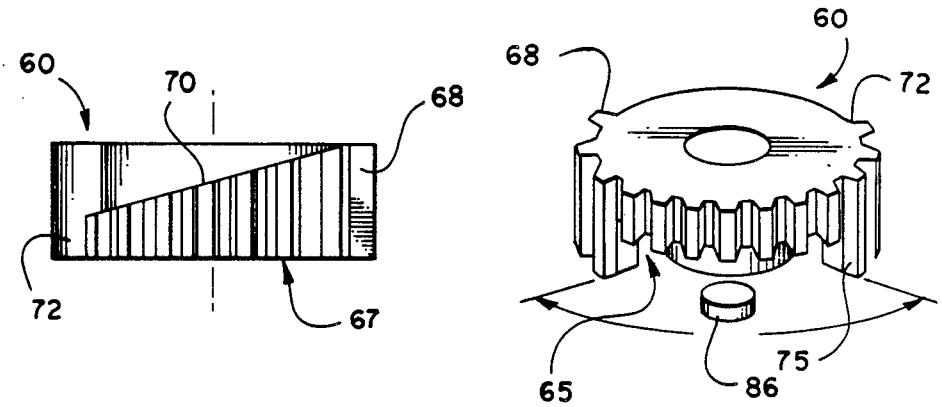
Fig_10   Fig_8

APPARATUS AND METHOD FOR SAFELY REMOVING NEEDLES FROM SYRINGES

TECHNICAL FIELD

The present invention relates to the disposal of blood contaminated needles attached using rotating connectors such as screw connectors or luer locks to syringes, and more particularly relates to an apparatus and method for removing such needles and depositing them into a container in a one-handed operation which greatly reduces the exposure of the user to being injured by the contaminated needle.

BACKGROUND ART

Each day, staggering quantities of disposable needles are used in hospitals, clinics, and physicians' offices. Many such needles are attached to syringes which are not discarded with the needles. For example, a syringe of the type sold under the trademark VACUUTAINER is used by securing a double needle to a needle retainer by screwing a threaded collar on the needle into a threaded opening in the end of the needle retainer. After the needle point outside the needle retainer is inserted into the patient's vein, a partially evacuated sample tube is forced onto the other needle point inside the retainer, and blood is sucked into the sample tube. The sample tube is removed and sent for analysis of its contents, and the needle retainer may be reused. Therefore, medical personnel typically remove the needle by unscrewing it, and place the needle in an approved disposal container.

Other types of syringes also use disposable needles with non-disposal suction devices. The needles may be connected by threaded screw connectors, luer locks, or the like. Disposable needles are typically fitted with plastic collars which have flange-like projections suitable for grasping with the fingers when twisting the needle into or out of the needle retaining portion of a syringe.

Personnel at hospitals and other medical facilities face a growing problem of safe disposal of needles because of the rise of diseases carried by the blood and other bodily fluids, such as AIDS. Manipulation of needle connectors after use can present a grave risk of being pricked by the exposed, contaminated needle. Attempts to insert the needle back into the protective sleeve provided for shipment create a similar risk. Past efforts to assist personnel in removing needles have reduced the danger somewhat, but have resulted in devices that are inconvenient to use. One such device is simply a container having a tapering slot in the top. The user holds the needle retainer, inserts the needle into the slot until the flanges of the collar are even with the slot, moves the needle into the smaller end of the slot until the flanges engage the slot, and twists the needle retainer to unscrew or unlock the needle, which falls into the container. This procedure has significant disadvantages. The user must position the needle carefully and supply the force necessary to rotate the needle retainer. Usually, the user must use two hands for the operation, one to steady the container, and one to manipulate the syringe and needle. This often results in the user laying down the used syringe for a time until both hands are available for removing the needle, rather than immediately placing the needle into a safe container. These disadvantages increase the opportunity and risk that a person will come into contact with the contaminated needle.

Thus, a need exists in the art for a needle removal system which can remove the disposable needle from the syringe with minimal non-precise manipulation of the needle and syringe using only one hand.

SUMMARY OF THE INVENTION

The present invention solves significant problems in the art by providing a needle removal apparatus and method according to which the user, touching only the needle retaining portion of the syringe, inserts the needle into a device which automatically rotates the needle to disconnect it from the syringe.

Generally described, the present invention provides an apparatus for removing needles of the type received in syringe bodies by way of a rotating connector, and defining a collar positioned outside the syringe body, comprising a needle guide housing defining an insert opening for receiving the needle; and means for engaging the collar and rotating the needle, such that the needle is released from the syringe. In the preferred embodiment of the invention, the means for rotating the needle comprises at least one disconnect wheel rotatably mounted adjacent to the insert opening, the wheel defining means at its periphery, facing the insert opening, for engaging the needle collar; and means for rotating the disconnect wheel in a disconnect direction responsive to downward movement of the needle into the insert opening.

Many disposable needles include a plurality of flanges extending outwardly from the collar, and in this case the means for rotating the needle preferably comprises at least one disconnect gear rotatably mounted adjacent to the insert opening with teeth facing the insert opening, so that the needle flanges engage the gear teeth. The needle guide housing may be mounted for movement within an actuator housing; and the means for rotating the gear may comprise a drive gear engaging the disconnect gear, with the drive gear defining a cam follower. A cam track is then position in the actuator housing to receive the cam follower and shaped so as to move the drive gear with respect to the disconnect gear as the needle guide housing moves within the actuator housing responsive to pressure exerted on the needle.

A needle removal apparatus according to the invention preferably includes a container adjacent to the needle rotating means for confining needles removed from syringes.

The present invention also provides a method of removing a needle from a syringe body to which the needle is attached by a rotating connector, generally comprising the steps of inserting the needle into an opening in a housing and engaging the syringe body against the housing; exerting pressure against the housing; and responsive to the pressure, rotating the needle sufficiently to release the needle from the syringe body.

Thus, it is an object of the present invention to provide an improved apparatus and method of removing needles from syringes and the like.

It is a further object of the present invention to provide a needle removal system which can be operated using one hand.

It is further object of the present invention to provide a needle removal system which does not require precise manipulation of the needle to achieve removal.

It is further object of the present invention to provide a needle removal system which presents little danger to the user.

It is further object of the present invention to provide a needle removal system which can be used quickly and conveniently.

Other objects, features, and advantages of the present invention will become apparent upon reading the following detailed description of embodiments of the invention, when taken in conjunction with the accompanying drawing and the appended claims.

BRIEF DESCRIPTION OF THE DRAWING

FIG. 1 is a pictorial view of a needle removal apparatus embodying the present invention.

FIG. 2 is a top plan view of the apparatus shown in FIG. 1.

FIG. 3 is an exploded view of the elements of the apparatus shown in FIG. 1.

FIG. 4 is a vertical cross sectional view taken along line 4—4 of FIG. 1.

FIG. 5 is a top view of the apparatus of FIG. 1, with the needle guide housing and actuator housing removed, and with parts broken away to show interior detail.

FIG. 6 is a side plane view of the circular drive gear.

FIG. 7 is a pictorial view of one of the disconnect gears.

FIG. 8 is a pictorial view of the disconnect gear of FIG. 7, taken from the opposite side.

FIG. 9 is a top plan view of the gear shown in FIG. 7.

FIG. 10 is a side plan view of the gear shown in FIG. 9, showing the ramp profile.

FIG. 14 is a diagrammatic side view of the same needle pushed far enough into the apparatus to disconnect the needle from the needle retainer.

FIG. 15 is a diagrammatic top view of the situation shown in FIG. 14.

FIG. 16 is a side view of a syringe assembly with portions broken away.

FIG. 17 is a bottom view of the syringe assembly of FIG. 16.

DETAILED DESCRIPTION

Figure 12:
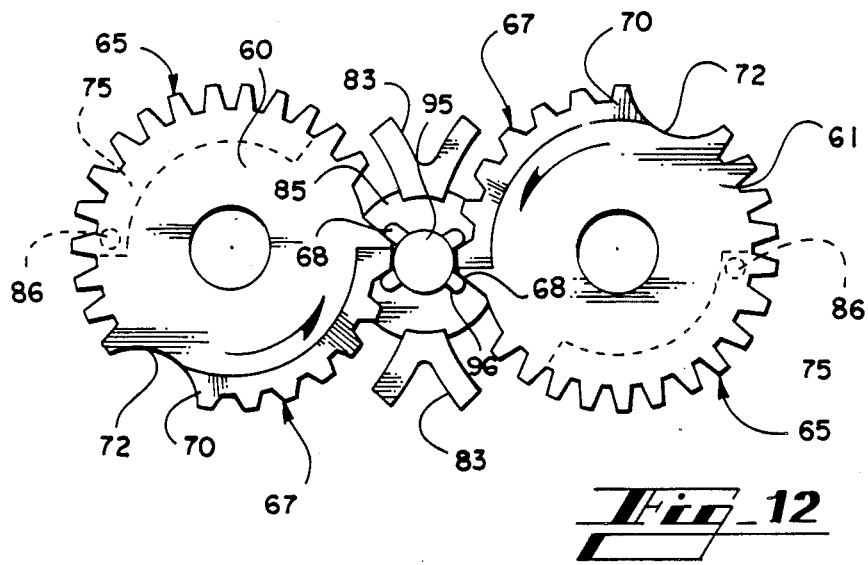
FIG. 12 is a diagrammatic top view of the situation shown in FIG. 11.

Referring now to the drawing, in which like numerals refer to like parts throughout the several views, FIG. 1 shows a needle removal apparatus 10 embodying the invention. The needle removal apparatus 10 is normally mounted in the mouth of a container 12, shown in dotted lines in FIG. 1. The container 12 may be a glass or plastic jar, for example. A syringe assembly 14 is shown in a position prior to insertion in the needle removal apparatus 10, and includes a needle 15 and a needle retainer portion 16. When the assembly 14 is inserted in the direction of the arrow, the parts of the needle removal apparatus described below automatically disconnect the needle 15 from the retainer 16.

Referring to FIGS. 1 and 2, the apparatus 10 includes an actuator housing 20, which is a cylinder open at both ends. Its top end is surrounded by an annular flange 21 which extends radially outwardly from the cylindrical wall. The housing 20 defines three vertical slots 22 which intersect the flange 21 and extend down to a point spaced above the bottom of the housing 20. The interior of the cylindrical wall defines three arcuate grooves 25 extending at an angle, preferably 40-60 degrees from the horizontal, from just under the flange 21 to the bottom of the housing 20. These grooves 25 form cam tracks or female screw threads to cause rotary motion, as described below.

Fitted for vertical motion within the actuator housing 20 is a needle guide housing 28, which is formed having a horizontal annular plate 29. As shown in FIG. 2, three tabs 30 extend outwardly from the circumference of the annular plate 29 and enter the slots 22 of the actuator housing 20. The tabs 30 thus prevent the housing 28 from rotating, but allow vertical movement. A cylindrical throat 31 rises from the center of the plate 29 and provides an initial guide way for a syringe assembly inserted into the apparatus 10. At the bottom of the throat 31, slightly below the plane of the plate 29, an annular shoulder 32 is formed around an insert opening 33, into which the needle 15 is placed. A pair gear shafts 34 and 35 extend vertically downward on opposite sides of the insert opening 33. The shafts terminate in lock posts 37 and 38, which are somewhat smaller in diameter than the shafts 34 and 35. The needle guide housing 28 also defines three spring stop tabs 40 which project downwardly near the periphery of the annular plate 29. The tabs 40 are spaced evenly around the plate 29.

Several other elements shown in FIG. 3 are connected to the needle guide housing 28 and move with it within the actuator housing 20. A drive gear 45 having a circular cross section fits around the gear shafts 34 and 35 and has a diameter slightly smaller than the inside diameter of the actuator housing 20, as shown in FIG. 4. The drive gear 45 defines an inner circular gear 47 adjacent the bottom surface 46 of the drive gear 45. A central bore 48 of diameter less than that of the circular teeth 47 is formed axially through the gear 45. In the annular space remaining, three arcuate spring tracks 50 are cut into the top surface 49 of the drive gear 45. These tracks 50 have a semicircular bottom profile which matingly receives the ends of the spring stop tabs 40 extending downwardly from the needle guide housing 28. Narrow walls 51 formed between the spring tracks 50 act as spring compression actuators in the manner described below. Coil springs 57 are placed within the tracks 50 between one of the walls 51 and one of the stop tabs 40, as shown in FIG. 5. Three balls 58 of plastic, Teflon, stainless steel, or other material are also placed in each track 50 on the other side of each tab 40 from the spring 57. The purpose of the balls is to provide spacing and reduce friction between the drive gear 45 and the needle guide housing 28. Those skilled in the art will understand that rounded nibs or projections extending from either element could provide these functions.

After the drive gear and springs are fitted under the needle guide housing 28, a pair of needle disconnect or unscrewing gears 60 and 61 are rotatably journalled on the gear shafts 34 and 35. The structure of these gears is best shown in FIGS. 7-10. The shafts 34 and 35 are received through central bores 63. An outer series of teeth 65 mesh with the teeth 47 of the drive ear 45, as shown in FIG. 5, and provide about 115 degrees of rotation of the disconnect gears 60 and 61 about the shafts 34 and 35. Two separate inner series of teeth 67, one on each of the gears 60 and 61, face each other across the space below the insert opening 33. The teeth 67 are formed differently from the teeth 65 for the specific purpose of engaging and unscrewing the needle, as explained below. The series 67 begins with an alignment tooth 68. A ramp 70 is cut out of the gears 60 and 61 through the arc of the teeth 67, beginning at about the center of the alignment tooth 68 and sloping downwardly to meet a dropout opening 72, positioned in the embodiment shown about 115 degrees from the alignment tooth. As explained in more detail below, the ramp accommodates portions of the needle assembly as it is unscrewed, and the dropout opening 72 allows the needle to drop vertically when it is fully unscrewed from the retainer 16.

The arcuate travel of the gears 60 and 61 is limited by rotation limiting cutouts 75 made in the lower portion of the outer series teeth 65. The ends of the cutouts 75 meet stops to be described below, and thereby stop motion of the gears when the dropout openings 72 are aligned with one another. The arcuate length of the teeth 67 determines how many turns of the needle are made before the dropout opening is reached, and this arcuate length may be varied in accordance with the number of turns needed to release the needle from the particular locking device being used. For example, a luer lock may require only a portion of a turn, whereas a conventional screw connector may require about 1.5 to 2 turns. Also affect by the required number of turns if the length of the outer series of teeth 65, which may be constructed to provide more or less than the 115 degrees of rotation described above.

A pair of coil springs 78 are placed on the shafts 34 and 35 under the gears 60 and 61. The springs 78 are for the purpose of allowing the gears to yield downwardly if the needle 15 is not fully seated in the needle retainer 16.

The final element of the needle removal apparatus 10 is a circular bottom plate 80, which includes an upwardly extending cylindrical wall 82 at the periphery of the plate 80. The bottom plate 80 defines a pair of openings 84 which receive the lock posts 37 and 38 at the ends of the shafts 34 and 35. A pair of flexible lock rings of conventional construction are forced onto the projecting lock posts to hold the bottom plate 80, and therefore the drive gear 45 and disconnect gears 60 and 61, in place beneath the needle guide housing 28. In this configuration, shown in FIG. 4, a pair of V-shaped spacers extend upwardly from the bottom plate to meet and support the housing 28 at the insert opening 33. These spacers also help to keep the needle in relatively straight axial orientation as it is being inserted between the gears 60 and 61. A central opening 85 is formed in the bottom plate 80 below the insert opening 33, to allow disconnected needles to drop out of the apparatus.

A pair of stops 86 extend upwardly from the bottom plate into the rotation limiting cutouts 75 of the gears 60 and 61. The stops 86 are positioned so that they are engaged by the gears when the dropout openings 72 in the gears are aligned. The cylindrical wall 82 is dimensioned to extend up to engage the bottom the drive gear 45, and positions the drive gear under the housing 28 without forcing the parts together so as to cause excess friction during rotation of the drive gear 45. The springs 78 urge the disconnect gears toward bearing surfaces on the bottom of the housing 28.

Further details of the assembled configuration may be perceived from FIG. 6, which is a view downwardly into the apparatus with the needle guide housing 28 removed. A vertical space for receiving the needle is bounded by the two disconnect gears 60 and 61, and the two spacers 83.

The needle removal apparatus is intended to be disposable after a period of use, such as when the container 12 is full. Thus, all of the elements described above are preferably made of suitable plastics known to those skilled in the art although metal can be utilized where appropriate.

Further details of the construction of a typical conventional syringe assembly 14 are shown in FIGS. 16 and 17. The needle 15 extends into a collar 95, which defines a plurality of outwardly extending flanges 96. The flanges terminate in a circular stop 97, which separated them from a threaded screw portion 98. The collar 95 is screwed into a tapped hole in the retainer portion 16 of the syringe 14, with an inner needle 99 (shown covered by a protective envelope) extending into the retainer 16. The flanges 96 are provided to allow the user to get a grip on the needle for screwing and unscrewing the needle. It is the object of the present invention to obviate the need for grasping the collar by hand to unscrew it after the needle is contaminated. The retainer portion 16 includes a leading surface 100, which engages the annular shoulder 32 within the needle guide housing 28.

Figure 11:
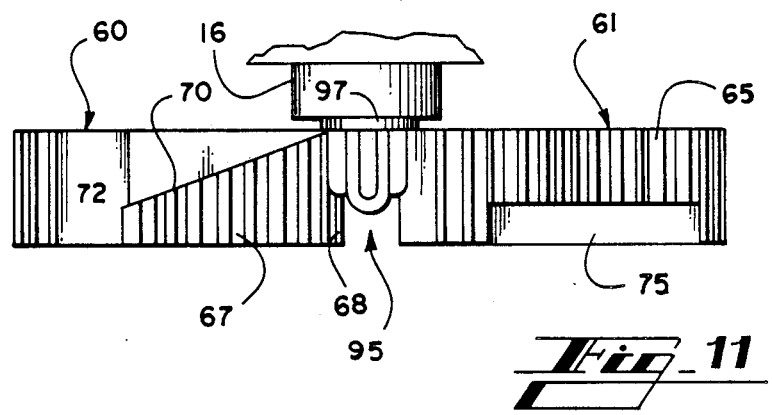
FIG. 11 is a diagrammatic side view of the disconnect gears and a needle initially inserted into engagement with the gears.

Operation of the needle removal apparatus is described as follows, with particular reference to FIGS. 11–15, which show a sequence of positions of the disconnect gears 60 and 61 during operation. After the syringe assembly 14 has been used and the needle 15 contaminated, the user simply takes the needle retainer 16 in one hand and inserts it into the throat 31 of the needle guide housing 28, until the needle 15 passes into the space between the disconnect gears, and the leading surface 100 of the retainer 16 is in contact with the annular shoulder 32. At this point, the flanges 96 have engaged the alignment teeth 68 of both gears 60 and 61, and have been caused to align the syringe so that the flanges are astride the alignment teeth as shown in FIGS. 11 and 12. The position of the syringe at this point in the operation is shown in dotted lines in FIG. 4.

Figure 13:
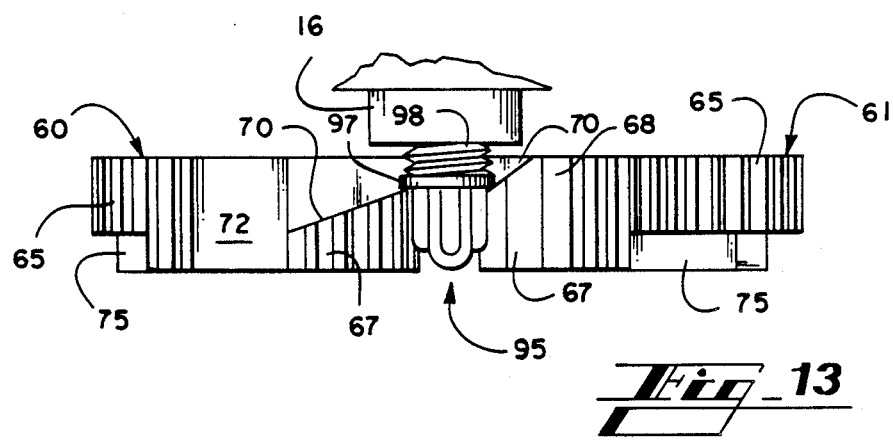
FIG. 13 is a diagrammatic side view of the same needle pushed further into the apparatus between the disconnect gears.

Detachment of the needle 15 from the retainer 16 is accomplished when the user asserts downward pressure on the retainer. This pressure causes the needle guide housing 28 to begin to move downwardly along the slots 22 in the actuator housing 20. As this occurs, the cam followers 55 of the drive gear 45 are forced to follow the path defined by the cam tracks 25 of the actuator housing 20. Thus, the drive gear 45 rotates counterclockwise as it descends with the needle guide housing 28, and its rotation causes the following other functions to be carried out. The rotating inner teeth 47 cause rotation of the disconnect gears 60 and 61, in turn causing the inner unscrewing teeth 67 to move relative to the flanges 96 of the needle collar 95. The teeth 67 engage the flanges 96 and turn the collar in an unscrewing direction (clockwise looking down as in FIGS. 12 and 15) as the gears turn. After a portion of the permitted rotation, the needle collar position is shown in FIG. 13. The threaded portion 98 has begun to emerge from the needle retainer 16. The ramp 70 provides room for the circular stop 97 to move downwardly past the gears, while the flanges remain engaged with the inner unscrewing teeth 67.

As the drive gear 45 rotates, it causes the spring compression walls 51 to compress the return springs 57 against the spring stops 40, which do not rotate. In the embodiment shown in FIG. 5, the springs are compressed through about 53 degrees of arc. At the same time, the balls 58 roll between the needle guide housing 28 and the spring tracks 50, in the space created by the departure of the adjacent wall 51 from its rest position.

When the rotation of the disconnect gears 60 and 61 has reached the configuration shown in FIGS. 14 and 15, the threaded portion 98 of the collar 95 has been completely unthreaded from the retainer 16, and the collar has moved down the ramp 70 into the dropout openings 72, which are now aligned across from one another. Thus, there is nothing to prevent the needle assembly from falling down through the opening 85 in the bottom plate, into the container 12. The ending position of the gears 60 and 61 is defined by the posts 86 on the bottom plate 80, which strike the ends of the cutouts 75 in the gears and prevent further rotation. This also prevents farther penetration of the needle guide housing, drive gear, and bottom plate into the actuator housing.

At this time, the user may terminate downward pressure on the needle retainer 16 and withdraw it from the throat 31. The energy stored in the compressed return springs 57 now causes the drive gear 45 to rotate in the opposite direction. The cam followers 55 climb back up the cam tracks 25, and the needle guide housing moves up the slots 22. The apparatus stops rotating, and reaches its original orientation as the balls 58 become trapped between the stops 40 and the walls 51. The alignment teeth 68 of the gears 60 and 61 are now reset across from one another ready to receive the next needle collar.

If the needle collar has not been fully screwed into the retainer, the circular stop 97 may engage the top of the gears 60 and 61 before the leading surface 100 meets the annular shoulder 32 of the needle guide housing. In this case, the springs 78 will allow the gears to yield downwardly, so that the flanges will still engage the teeth 68 and the retainer will transmit pressure to the needle guide housing.

It should be understood that the return function provided by the return springs 57 could be performed by compression springs mounted below the bottom plate 80 to urge the assembled parts upwardly when pressure is released. It should also be understood that the needle collar could be engaged for unscrewing by means other than gear teeth. For example, the disconnect gears could be wheels having resilient outer bands for frictionally engaging the needle and/or the interior of the drive gear, which could also be lined with a high friction interface rather than gear teeth. Alternately, the needle collar could be rotated by a rack or racks caused to move past the collar.

While this invention has been described in detail with particular reference to preferred embodiments thereof, it will be understood that variations and modifications can be effected within the spirit and scope of the invention as described hereinbefore and as defined in the appended claims.

What is claimed is:

1. An apparatus for removing needles of the type received in syringe bodies by way of a rotating connector, and defining a collar positioned outside said syringe body, comprising:
   a needle guide housing defining an insert opening for receiving said needle;
   means for movable supporting said needle guide housing; and
   means drivingly linked to said needle guide housing and driven by force exerted on said guide housing parallel to the length of said needle for engaging said collar and rotating said needle when said needle is received in said insert opening, such that said needle is released from said syringe.

2. The apparatus of claim 1, further comprising a container positioned adjacent to said needle rotating means for confining needles removed from syringes.

3. The apparatus of claim 1, wherein said needle includes a plurality of flanges extending outwardly from said collar, and wherein said means for rotating said needle comprises:
   at least one disconnect gear rotatably mounted adjacent to said inset opening with teeth facing said insert opening, said gear teeth positioned for engaging said needle flanges; and
   means for rotating said gear in a disconnect direction responsive to downward movement of said needle into said insert opening.

4. The apparatus of claim 1, wherein said means for rotating said needle comprises:
   at least one disconnect wheel rotatably mounted adjacent to said insert opening, said wheel defining means at its periphery facing said insert opening, for engaging said needle collar; and
   means for rotating said disconnect wheel in a disconnect direction responsive to downward movement of said needle into said insert opening.

5. An apparatus for removing needles of the type received in syringe bodies by way of a rotating connector, and defining a collar including a plurality of flanges extending outwardly therefrom positioned outside said syringe body, comprising:
   a needle guide housing, defining an insert opening for receiving said needles, mounted for movement within an actuator housing;
   at least one disconnect gear rotatably mounted adjacent to said insert opening with teeth facing said insert opening, said gear teeth positioned for engaging said flanges extending outwardly from said collar;
   a drive gear engaging said disconnect gear, said drive gear defining a cam follower; and
   a cam track positioned in said actuator housing to receive said cam follower and shaped so as to move said drive gear with respect to said disconnect gear as said needle guide housing moves downwardly within said actuator housing responsive to pressure exerted on said needle.

6. The apparatus of claim 5, wherein said disconnect gear defines a ramp cut out of its teeth in the path of said flanges, said ramp extending around a portion of the periphery of said disconnect gear and terminating in a discharge opening through which said needle passes after being rotated sufficiently to release from said syringe body.

7. The apparatus of claim 6, wherein said means for rotating said needle includes a pair of said disconnect gears rotatably mounted on said needle guide housing with their peripheries on opposite sides of said insert opening; and means for orienting said disconnect gears such that the upper end of said ramp of each of said gears is adjacent to said insert opening prior to insertion of said needle.

8. The apparatus of claim 7, wherein said drive gear comprises a circular gear with inwardly directed teeth surrounding said two disconnect gears, said circular gear being rotated about said disconnect gears as said cam follower moves along said cam track.

9. The apparatus of claim 8, further comprising means for returning said circular gear to its starting position following said rotation about said disconnect gears.

10. The apparatus of claim 5, further comprising means for returning said drive gear to its starting position following said movement responsive to pressure exerted on said needle.

11. An apparatus for removing needles of the type received in syringe bodies by way of a rotating connector, and defining outwardly extending flanges positioned outside said syringe body, comprising:
   a cylindrical actuator housing defining a cam track in the cylindrical wall thereof;
   a needle guide housing defining an insert opening along the axis of said actuator housing for receiving said needle, and a shoulder for engaging said syringe body, said needle guide housing being mounted for sliding movement axially within said actuator housing;
   a pair of disconnect gears rotatably mounted on said needle guide housing about axes parallel to the axis of said actuator housing, with the peripheral teeth of said gears passing closely adjacent to opposite sides of said insert opening so as to engage said needle flanges when said needle is inserted, each of said gears defining a ramp cut into said gear teeth in the path of said needle flanges around a portion of the periphery of said disconnect gear, said ramp terminating in a discharge opening;
   a circular drive gear surrounding said disconnect gears, said drive gear defining a cam follower engaging said cam track in said actuator housing;
   said cam track causing said drive gear rotate upon motion of said needle guide housing into said actuator housing, thereby causing rotation of said disconnect gears so as to rotate said needle and disconnect it from said syringe body; and
   means for rotating said drive gear in the opposite direction to return said disconnect gears to their original orientation and to move said needle guide housing to its original position.

12. A method of manually removing a needle from a syringe body to which the needle is attached by a rotating connector, comprising the steps of:
   inserting said needle into an opening in a movably supported needle guide housing and engaging said syringe body against said needle guide housing;
   moving said needle guide housing by exerting pressure upon said syringe body and thereby against said needle guide housing; and
   driving said needle in a rotating motion by drivingly linking said movement of said needle guide housing to a means for rotating said needle, said rotating motion being sufficient to release said needle from said syringe body.

13. A manually-operated apparatus for one-handed removal of needles of the type received in syringe bodies by way of a rotating connector, and defining a collar positioned outside said syringe body, comprising:
   a needle guide housing defining an insert opening for receiving said needle;
   means for movably supporting said needle guide housing; and
   means drivingly linked to said needle guide housing and driven by force exerted on said guide housing parallel to the length of said needle for engaging said collar and rotating said needle when said needle is received in said insert opening, such that said needle is released from said syringe.

14. An apparatus for removing needles of the type received in syringe bodies by way of a rotating connector, and defining a collar positioned outside syringe body, comprising:
   a needle guide housing mounted for movement within an actuator housing and defining an insert opening for receiving said needle; and
   means positioned adjacent to said insert opening for rotating said needle responsive to movement of said needle guide housing with respect to said actuator housing.

15. The apparatus of claim 14, wherein said means for rotating said needle comprises:
   a pair of disconnect gears rotatably mounted on said needle guide housing with their peripheries on opposite sides of said insert opening; and
   means for rotating said disconnect gears responsive to downward movement of said needle into said insert opening.

16. The apparatus of claim 15, wherein said means for rotating said disconnect gear comprises:
   a cam track defined in the cylindrical wall of said actuator housing;
   a circular drive gear engaging said disconnect gears, said drive gear defining a cam follower;
   said cam follower engaging said cam track in said actuator housing; and
   said cam track causing said drive gear to rotate upon motion of said needle guide housing into said actuator housing, thereby causing rotation of said disconnect gears so as to rotate said needle and disconnect it from said syringe body.

17. An apparatus for removing needles of the type received in syringe bodies by way of a rotating connector, and defining a collar positioned outside said syringe body, comprising:
   carriage for defining an insert opening for receiving said needle;
   means for movably supporting said carriage; and
   means drivingly linked to said carriage and driven by force exerted on said carriage parallel to the length of said needle for engaging said collar and rotating said needle when said needle is received in said insert opening such that said needle is released from said syringe.

18. The apparatus of claim 17, wherein said carriage is mounted for movement along a path parallel to the axis of said opening.

19. The apparatus of claim 17, further comprising a container positioned adjacent to said needle rotating means for confining needles removed from syringes.

20. The apparatus of claim 17, wherein said means for rotating said needles comprises:
   at least one disconnect wheel rotatably mounted adjacent to said insert opening, said wheel defining means at its periphery facing said insert opening, for engaging said needle collar; and
   means for rotating said disconnect wheel in a disconnect direction responsive to downward movement of said needle into said insert opening.

* * * * *